United States Patent [19]

Su et al.

[11] 4,329,336

[45] May 11, 1982

[54] NONIONIC BASED ANTIMICROBIAL SHAMPOO

[75] Inventors: Dean T. Su, North Brunswick; Warren R. Schubert, Somerset, both of N.J.

[73] Assignee: Colgate-Palmolive Company, New York, N.Y.

[21] Appl. No.: 205,560

[22] Filed: Nov. 10, 1980

[51] Int. Cl.$^3$ .......................... A61K 7/06; A61K 7/09; A61K 31/415

[52] U.S. Cl. ........................................ 424/70; 424/71; 424/273 R; 424/DIG. 4; 252/106; 252/DIG. 13

[58] Field of Search ......... 424/70, 71, 273 R, DIG. 4; 252/DIG. 13, 106

[56] References Cited

U.S. PATENT DOCUMENTS 3,812,142  5/1974  Meiser et al. ..................... 424/269
3,903,287  9/1975  Meiser et al. ..................... 424/273 R
4,154,706  5/1979  Kenkare et al. ............ 252/DIG. 13

FOREIGN PATENT DOCUMENTS 1502144  2/1978  United Kingdom .

Primary Examiner—Donald B. Moyer
Attorney, Agent, or Firm—Richard N. Miller; Murray M. Grill; Herbert S. Sylvester

[57] ABSTRACT

A homogeneous liquid nonionic based antimicrobial conditioning shampoo which includes about 0.5 to 2.5% of the antimicrobial agent, 1-imidazolyl-1-(4-chlorophenoxy)-3,3-dimethylbutan-2-one, solubilized in an aqueous solution of critical amounts of a four component mixture of the following specific non-ionic ingredients:

a. about 2–20% by weight of a polyoxyethylene hexitan mono-higher fatty acid ester,
b. about 4–10% by weight of a tertiary amine oxide,
c. about 1–7% by weight of a fatty acid mono- or di-ethanolamide,
d. about 0.05–1.0% by weight of a polyacrylamide having a molecular weight of 100,000 to 3,000,000. This shampoo is transparent in appearance and should preferably contain 65–80% water.

7 Claims, No Drawings

NONIONIC BASED ANTIMICROBIAL SHAMPOO

This invention relates to a nonionic based antimicrobial shampoo containing the water-insoluble antimicrobial agent, 1-imidazolyl-1-(4-chlorophenoxy)-3,3-dimethylbutan-2-one, solubilized in an aqueous solution of critical amounts of specific nonionic components, capable of both cleansing and conditioning the hair in a single operation, by simply washing the hair therewith.

PRIOR ART

The prior art antidandruff shampoos contain organozinc compounds such as zinc pyrithione, which is not soluble in a liquid shampoo, resulting in a potentially non-homogeneous, milky shampoo wherein the insoluble antidandruff agent is unevenly dispersed in and/or precipitates out of the shampoo composition.

The imidazolyl ketones such as 1-imidazolyl-1-(4 chlorophenoxy)-3,3-dimethylbutan-2-one, are disclosed in U.S. Pat. Nos. 3,812,142 and 3,903,287 as antimycotic agents, useful in pharmaceutical compositions including aqueous suspensions containing surface active agents such as polyoxyethylene sorbitan fatty acid esters. British Pat. No. 1,502,144 and its German counterpart, Pat. No. 2,430,039, disclose cosmetic compositions such as shampoos containing the imidazolyl ketone antimycotic agents dispersed in a dermatologically acceptable carrier which contains a detergent-active compound. The shampoos are in the form of creams, aerosols, powders and liquids. Although non-ionic, amphoteric and cationic surfactants are listed, the specific liquid shampoos disclosed contain 50% anionic surfactant and 3.5–5% of the non-ionic fatty acid diethanolamide. German Pat. No. 2,600,800 discloses the 1-imidazolyl-1-(4-chlorophenoxy)-3,3-dimethylbutan-2-one in a fungicidal composition, which may be in the form of a dispersion in water, as useful for protecting plaster coatings, dispersion dyes, wall-paper, tiled surfaces, paints, glues, bitumina, furniture, leather, shower curtains, textiles, carpets, wood and paper. German Pat. No. 2,700,806 also discloses a mixture of the imidazolyl ketone fungicide and a quaternary ammonium bactericide useful for protecting materials such as paints, glues, bitumen, cellulose, paper, textiles, leather and wood.

Although the prior art discloses the specified imidazolyl ketone as an antimycotic agent, and its use in various formulations including shampoos, said liquid compositions are usually in the form of suspensions and/or dispersions. When in suspension form, this is due to the water-insolubility property of the imidazolyl ketones which results in opaque and milky non-homogeneous liquid shampoos, similarly to the organozinc-containing shampoos.

In addition to the anti-mycotic agent, shampoos, must include surfactants, usually based on anionic detergents, as shown in aforedescribed British Pat. No. 1,502,144. However, non-ionic and/or amphoteric detergents may be subsituted for all or part of said anionic detergents as shown by U.S. Pat. No. 4,009,256, wherein the aqueous shampoo composition comprises 1–25% amphoteric agent such as the imidazoline derivatives or the amido betaines, plus 0–20% of either a nonionic surfactant such as the amine oxides or an anionic surfactant. An all non-ionic liquid shampoo is disclosed in U.S. Pat. No. 4,154,706, containing three non-ionic components: an amine oxide, a polyethoxylated hexitan ester and either a higher alkoxy polyoxyethylene ethanol or an alkyl glycoside or a mixture thereof, or a 5–6 component composition, wherein a polyacrylamide and an alkanolamide may be added to the three component system or substituted for the polyoxyethylene ethanol or alkyl glycoside component. U.S. Pat. No. 3,953,382 discloses a nonionic based detergent composition for washing fabrics consisting of a ternary mixture of a water-soluble polyetheneoxy organic nonionic detergent, a water-insoluble polyalkyleneoxy nonionic compound and an alkanolamide or tertiary amine oxide or sulfoxide. U.S. Pat. No. 4,013,787 further discloses a film forming cationic polymer conditioning agent in cosmetic hair compositions including nonionic based or cationic based or anionic based liquid shampoos.

However, there is no disclosure of the imidazolyl ketone antimicrobial agent solubilized in a nonionic based aqueous conditioning shampoo.

DESCRIPTION OF THE INVENTION

It has now been found that a mixture of specified nonionic components in critical amounts solubilizes the insoluble imidazolyl ketone in an aqueous solution in the production of a homogeneous liquid, antimicrobial, conditioning shampoo.

Accordingly, it is an object of present invention to provide a homogeneous liquid antimicrobial shampoo.

Another object of this invention is to provide a liquid shampoo capable of both cleansing and conditioning the hair in a single operation.

Still another object of this invention is to provide an aqueous liquid antimicrobial shampoo containing 1-imidazolyl-1-(4-chlorophenoxy)-3,3-dimethylbutan-2-one solubilized in said aqueous medium.

Another object of this invention is to provide a nonionic based shampoo capable of solubilizing the aforesaid imidazolyl ketone antimicrobial agent in the production of a clear homogeneous liquid shampoo.

Other objects of this invention will become apparent to those skilled in the art upon reading the following specification.

Accordingly, the present invention relates to a homogeneous liquid nonionic based, antimicrobial, conditioning shampoo containing an effective antimicrobial amount of 1-imidazolyl-1-(4-chlorophenoxy)-3,3-dimethylbutan-2-one solubilized in an aqueous vehicle containing a polyoxyethylene hexitan mono-higher fatty acid ester, a tertiary amine oxide, a fatty acid mono- or di-ethanolamide, and a polyacrylamide having a molecular weight of 100,000 to 3,000,000 as the essential nonionic components in certain specified amounts.

The antimicrobial agent utilized in the instant invention is 1-imidazolyl-1-(4-chlorophenoxy)-3,3-dimethylbutan-2-one having the structural formula:

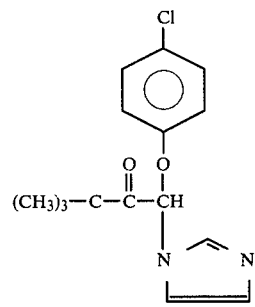

which is prepared by reacting 1-bromo-1-(4-chlorophenoxy)-3,3-dimethylbutan-2-one with imidazole dissolved in acetonitrile as disclosed in U.S. Pat. Nos. 3,812,142 and 3,903,287, which are made a part of this specification. This imidazolyl ketone is a water insoluble crystalline powder having a melting point of 94.5°–97.8° C. which may be obtained from the Bayer Company.

Solubility studies using 2 g. of the imidazolyl antimicrobial agent plus 5 g. polyoxyethylene (20) sorbitan mono-laurate (Tween 20) or 5 g. lauric myristic diethanolamide (LMDEA) or mixtures of 4, 3, 2, 1 g. Tween 20 and 1, 2, 3, 4, g. LMDEA respectively in 93 g. of water, wherein the resultant liquid was cloudy and the ingredients separated out. Similarly, poor solubility results were obtained by combining 3.5 g. of a solution of 100 g. imidazolyl ketone agent in 250 g. LMDEA, with 16.7 g. myristyl dimethylamine oxide (30% active) (MO) in 79.8 g. water, or with 8.4 g. MO in 88.1 g. water, or with 3.3 g. MO in 92.2 g. water wherein the resultant products were cloudy with fine precipitates. On the other hand, when 3.5 g. of the aforedefined imidazolyl solution in LMDEA was mixed with 33.3 g. MO in 63.2 g. water, a clear solution was obtained. This 33.3 g. MO represents a 10% active content, whereas the cloudy products represent 5%, 2.5% and 1% active concentrations respectively. Thus, it is apparent that the amounts and specificity of ingredients are critical in order to solubilize the antimicrobial imidazolyl compound in an aqueous medium in order to obtain a clear shampoo. It is noted that all of the test compounds are nonionic surface active agents.

It has additionally been found that this antimicrobial agent is also nonionic as a result of stearic hindrance effects. The effective concentration of this agent useful in present aqueous shampoo vehicle is preferably about 0.5–2.5% by weight of the total shampoo.

Accordingly, the shampoo vehicle constitutes about 65–80% water containing critical amounts of specifically essential nonionic compounds to effect an aqueous vehicle for dissolution of the aforesaid antimicrobial agent.

The essential nonionic components contained in this shampoo comprise a polyethoxylated hexitan fatty acid ester, a tertiary amine oxide, a higher fatty acid enthanolamide and a polyacrylamide having an average molecular weight of 100,000 to 3,000,000 in certain critical amounts in order to avoid precipitation of the antimicrobial agent.

More specifically, the instant antimicrobial shampoo is based on four nonionic components comprising about 2–20% by weight of a polyoxyethylene hexitan mono-higher fatty acid ester having 4 to 100 moles of ethylene oxide per mole, about 4–10% by weight of dimethyl higher alkyl tertiary amine oxide, about 1–7% by weight of a higher fatty acid mono- or di-ethanolamide, and about 0.05–1.0% of a polyacrylamide having an average molecular weight of 100,000 to 3,000,000.

The polyoxyethylene hexitan mono-higher fatty acid ester component of present liquid shampoo provides cleaning action and functions as a dispersant. The useful compounds in this group include esters having from 10–20 carbon atoms in the higher fatty acyl thereof and 4–100, preferably 10–80 mols of ethylene oxide per mol. Preferably, the hexitan is sorbitan, although mannitan and other hexitans are also often useful, the higher fatty acyl will be of 10–16 or 20 carbon atoms, more preferably of 12–16 or 18 carbon atoms and most preferably of about 12 carbon atoms, and the number of ethoxies will be from 15–80, often preferably about 20. Especially useful is an I.C.I. product sold under the trade name Tween 20, also known as polysorbate 20. Similarly useful products are sold under similar identifications, such as Tweens 40, 60, and 80, all of which are nonionic surface active agents wherein the higher fatty acyl is palmitoyl, stearoyl or oleyoyl and the number of the mols of ethylene oxide per mol is about 20. However, of these materials the polyoxyethylene (20) sorbitan monolaurate of the Polysorbate 20 type is usually favored. Polyoxyethylene 80 (mol) sorbitan monolaurate may be substituted in place of polysorbate 20.

The amine oxide component of instant liquid shampoo provides both cleaning and conditioning properties to the shampoo, and is nonionic in the pH range of the shampoo, which is normally within the range of 6.5 to 7.5 and preferably 6.8 to 7.3 or about 7. The amine oxides useful herein have the structural formula:

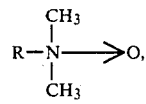

wherein R is an alkyl radical of 10–16 carbons. Examples of suitable amine oxides include dimethyl laurylamine oxide, dimethyl cetylamine oxide and dimethyl myristylamine oxide. Of course, as with the other components of the present composition, the amine oxides will usually be chosen for desired solubility in the aqueous medium employed and for compatibility with the other components of the shampoo.

The ethanolamide component of instant liquid shampoo functions primarily as a foam booster. Useful compounds in this group include mono- and di-ethanolamides of higher fatty acids having about 10–18 carbon atoms. Specific examples of suitable ethanolamides include cocomonoethanolamide, cocodiethanolamide, lauric myristic diethanolamide, lauric monoethanolamide, or combinations thereof.

The polyacrylamide component of instant liquid shampoo functions as a thickening agent to increase the viscosity of the aqueous shampoo, which may be between the consistency of honey and that of water. The polyacrylamide useful herein has an average molecular weight of 100,000 to 3,000,000, and has been described in U.S. Pat. No. 3,001,949. This component, like all the other nonionic components are water-soluble and remain water-soluble during storage of the shampoo.

This particular combination of hexitan fatty-acid monoester, amine oxide, ethanolamide and polyacrylamide provides a balanced, completely nonionic surface active system which solubilizes the antimicrobial agent and has desirable foaming, lathering, detersive and conditioning properties, as well as desirable viscosity characteristics. The resultant homogeneous liquid shampoo is capable of both washing and conditioning the hair in a single operation by simply shampooing. An additional and essential function of instant nonionic-based shampoo is the concomitant antimicrobial action afforded by the specific imidazolyl ketone.

In addition to the previously mentioned constituents of the liquid shampoo one may also employ normal and conventional adjuvants, provided they do not adversely affect the properties of the shampoo. Thus, there may be used various coloring agents and perfumes; ultraviolet light absorbers such as the Uvinuls, which are products of GAF Corporation; preservatives such as formaldehyde or hydrogen peroxide; pearlescing agents and opacifiers; solvents, such as ethanol, preferably in the form of a specially denatured alcohol, and glycols (ethylene glycol is useful as a clarifying agent, to prevent high and low temperature clouding of desirably clear shampoos); lubricants, such as mineral oil and higher fatty alcohols, e.g., cetyl alcohol, stearyl alcohol; quaternary antibacterial materials; viscosity modifiers such as polyethylene glycol distearate of a molecular weight in the range of 2000–8000; etc. The proportion of such adjuvant materials, in total, will normally not exceed 5% of the shampoo, and preferably less than 2% thereof. The percentages of most of such individual components will be less than 2% and preferably less than 1%.

Another additional component suitable in this type of formulation is a cationic quaternized polymer formed by the reaction of dimethyl sulfate with a copolymer of vinyl pyrrolidone and dimethyl aminoethylmethacrylate (Gafquat 755-GAF Corporation) which are water soluble, in minor amounts up to about 2% by weight.

The present shampoos are readily made by simple mixing methods from readily available components which, on storage, do not adversely affect the entire composition. Thus, the products are capable of being made in desired clear form or in opaque or opalescent form. The viscosities are adjustable by changing the total percentage of active ingredients and by modifying the percentages of polyacrylamide and other adjuvants. In all such cases the product made will be pourable from a relatively narrow mouth bottle (1.5 cm. diameter) and the shampoo will not be so thin as to run off the hair or hands. The viscosity of the shampoo will normally be about that of glycerin at room temperature, e.g., about 1,000 centipoises, but the viscosity may be in the broader ranges of 250–2,000 and 50–5,000 centipoises. Its viscosity may approximate those of commercially acceptable shampooes now on the market. Instead of measuring viscosity directly, as by a Brookfield LVF viscosimeter, one may employ standard laboratory flow tests, in which flow times through a restriction or tube length under a reproducible head are measured in seconds, utilizing a Raymond tube. Viscosities may range from 10–80 seconds. The shampoo viscosity and the shampoo itself remain stable on storage for lengthy periods of time, without color changes or settling out of any insoluble materials.

These products have unexpectedly desirable properties. For example, the foam quality and lubricity are comparable to standard shampoos based on triethanolamine lauryl sulfate. Further, such shampoos clean the hair exceptionally well and leave it easy to comb, manageable and of low raspiness, are less drying, leaving the hair with a softer feel, producing fewer split ends after shampooing, and being easier to comb and causing less flyaway effect.

The following examples illustrate but do not limit the invention. Unless otherwise mentioned, all percentages in the examples and elsewhere in the specification are by weight and all temperatures are in °C.

Clear Antimicrobial Shampoos

EXAMPLE 1

| | % |
|---|---|
| Polysorbate 20 (polyoxyethylene (20) sorbitan monolaurate) | 17.67 |
| Dimethyl myristylamine oxide | 7.00 |
| Cocomonoethanolamide (CMEA) | 2.00 |
| Polyethylene glycol distearate (6000 mol wt.) | 1.90 |
| Climbazole (Bayer Company) (1-imidazolyl-1-(4-chlorophenoxy)-3,3-dimethylbutan-2-one) | 0.50 |
| Deionized water (D. I. water) | 69.70 |
| Separan NP-10 (water soluble polyacrylamide of mol wt. 1,500,000 mfd by Dow Chemical Co.) | .20 |
| Uvinul 490 (ultraviolet light absorber) | 0.03 |
| Perfume | 1.00 |

Climbazole was first dissolved in the polysorbate 20 at 45° C., to which was then added the cocomonoethanolamide, followed by the dimethyl myristylamine oxide and then the polyethylene glycol distearate while agitating the mixture. The Separan NP-10 is dissolved in the water and added to said mixture with agitation. The perfume and Uvinul 490 are subsequently admixed with the composition.

The resultant product is an excellent conditioning shampoo of desired viscosity, foaming power, foam stability, antimicrobial activity and good shampooing effects, i.e., leaves the wet hair easy to comb, with a soft feel and static free.

In the shampooing described herein and in subsequent examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE 2

Example 1 is repeated except that the imidazolyl compound content is increased to 1% and the water content is reduced to 69.20%.

EXAMPLE 3

Example 1 is repeated except that the imidazolyl compound content is increased to 1.5% and the water content reduced to 68.70%.

EXAMPLE 4

Example 1 is repeated except that the imidazolyl compound content is increased to 2% and the water content reduced to 68.20%.

EXAMPLE 5

Example 4 is repeated except that the 1% perfume is omitted and the water content increased to 69.20%.

EXAMPLE 6

Example 3 is repeated without the 1% perfume and the water content increased to 69.70%.

The products of Examples 2–6 possess similarly good antimicrobial, cleansing and conditioning properties.

EXAMPLE 7

|  | % |
| --- | --- |
| Polysorbate 20 | 17.60 |
| Ammonyx MO (dimethyl myristylamide oxide) | 7.00 |
| CMEA | 2.00 |
| Polyethylene glycol distearate (6000 mol wt.) | 1.90 |
| Climbazole | 2.00 |
| Separan NP-10 | 0.20 |
| Perfume | 1.00 |
| Uvinul 490 | 0.03 |
| D & C Green No. 5 | 0.15 |
| D & C Green No. 10 | 0.40 |
| D. I. water | 67.72 |

This shampoo is prepared in accordance with the process described in Example 1, except that the dyes are sequentially added to the composition. The resultant product is a clear green liquid shampoo with a viscosity of 40 sec.

EXAMPLE 8

|  | % |
| --- | --- |
| Polysorbate 20 | 17.10 |
| Ammonyx MO | 6.75 |
| CMEA | 1.91 |
| Polyethylene glycol distearate (6000 mol wt.) | 2.75 |
| Climbazole | 2.00 |
| Separan NP-10 | 0.275 |
| Perfume | 1.000 |
| Uvinul 400 | 0.03 |
| Formalin (formaldehyde) | 0.10 |
| D & C Orange No. 4 (1%) | 0.025 |
| D & C Red No. 33 | 0.025 |
| D. I. water | 68.035 |

This shampoo is prepared in accordance with the procedure of Example 1 except that the formalin and dyes are sequentially admixed with the composition to produce the final shampoo, which is a clear reddish liquid having a viscosity of 40.7 sec.

All of the aforedefined shampoo formulations were of useful viscosity, and possessed good foaming properties, antimicrobial activity, cleaning efficacy and conditioning properties. Hair shampooed with these compositions felt exceptionally clean, was easy to comb and manageable.

Variations in the above formulations may be made. For example, other amine oxides may be substituted for the dimethyl myristylamine oxide such as the dimethyl laurylamine oxide, dimethyl cetyl amine oxide and the like. Similarly other ethanolamides may be substituted for the cocomonoethanolamide such as cocodiethanolamide, lauric myristic diethanolamide and the like. The specified polyacrylamide may be replaced by other polyacrylamides.

Likewise, the amounts of each of the nonionic components may be varied within the designated percentage aforedefined without adversely affecting the solubility of the antimicrobial agent.

The invention has been described with respect to various examples and embodiments but is not to be limited to these because it is evident that one of skill in the art with the present application before him will be able to utilize substitutes and equivalents without departing from the spirit of the invention.

We claim:

1. A homogeneous, liquid, nonionic based, antimicrobial, conditioning shampoo containing about 0.5–2.5% of 1-imidazolyl-1-(4-chlorophenoxy)-3,3-dimethyl butan-2-one solubilized in an aqueous vehicle, wherein the aqueous vehicle constitutes about 65–80% by weight of water containing four nonionic components comprising about 2–20% by weight of a polyoxyethylene hexitan mono-higher fatty acid ester having 10–20 carbon atoms in the higher acyl thereof and 10–80 mols ethylene oxide per mol, about 4–10% by weight of a dimethyl higher alkyl amine oxide having 10–16 carbons in the higher alkyl thereof, about 1–7% by weight of a higher fatty acid mono- or di-ethanolamide, and about 0.05–1.0% weight of a water-soluble polyacrylamide having an average molecular weight of 100,000 to 3,000,000.

2. A shampoo in accordance with claim 1, wherein the polyoxyethylene hexitan monoester is polyoxyethylene sorbitan monolaurate containing 20 mol ethylene oxide per mol.

3. A shampoo in accordance with claim 2, wherein the amine oxide is dimethyl myristylamine oxide.

4. A shampoo in accordance with claim 3, wherein the ethanolamide is cocomonoethanolamide.

5. A shampoo in accordance with claim 1, wherein the shampoo is a clear liquid.

6. A shampoo in accordance with claim 1, which includes up to 2% by weight of a cationic quaternized polymer, wherein said cationic polymer is the reaction product of dimethyl sulfate with the copolymer of vinylpyrrolidone and dimethylaminoethylmethacrylate.

7. A method of simultaneously cleansing and conditioning hair which comprises shampooing with the composition of claim 3.

* * * * *